US008513278B2

(12) United States Patent
Somberg

(10) Patent No.: US 8,513,278 B2
(45) Date of Patent: Aug. 20, 2013

(54) PARENTERAL DEXTROSE FORMULATION OF CLOPIDOGREL

(71) Applicant: Academic Pharmaceuticals Incorporated, Lake Bluff, IL (US)

(72) Inventor: John C Somberg, Lake Forest, IL (US)

(73) Assignee: Academic Pharmaceuticals, Inc., Lake Bluff, IL (US)

( * ) Notice: Subject to any disclaimer, the term of this patent is extended or adjusted under 35 U.S.C. 154(b) by 0 days.

(21) Appl. No.: 13/684,785

(22) Filed: Nov. 26, 2012

(65) Prior Publication Data
US 2013/0137716 A1 May 30, 2013

Related U.S. Application Data

(60) Provisional application No. 61/563,770, filed on Nov. 26, 2011.

(51) Int. Cl.
*A61K 31/44* (2006.01)

(52) U.S. Cl.
USPC .......................................................... 514/301

(58) Field of Classification Search
USPC ............................................................ 514/301
See application file for complete search history.

(56) References Cited

U.S. PATENT DOCUMENTS

| | | | |
|---|---|---|---|
| 5,576,328 | A | 11/1996 | Herbert et al. |
| 5,989,578 | A | 11/1999 | Bernat et al. |
| 7,148,211 | B2 | 12/2006 | Mazess et al. |
| 7,923,447 | B2 | 4/2011 | Somberg et al. |

*Primary Examiner* — Raymond Henley, III
(74) *Attorney, Agent, or Firm* — Vance Intellectual Property PC

(57) ABSTRACT

Described herein are ways to solubilize clopidogrel for parenteral administration containing clopidogrel and $D_{50}W$, which is useful in the prevention of platelet aggregation in acute coronary syndrome, acute myocardial infarction or to prevent platelet facilitated thrombosis following coronary angioplasty and/or coronary stenting.

20 Claims, No Drawings

US 8,513,278 B2

PARENTERAL DEXTROSE FORMULATION OF CLOPIDOGREL

FIELD OF THE INVENTION

This invention relates to new parenteral dextrose-based formulations of clopidogrel, a very insoluble anti-platelet agent.

BACKGROUND OF THE INVENTION

Many lipophilic anti-platelet agents such as clopidogrel are only sparingly or negligibly water-soluble. The poor water-solubility of these agents often results in major difficulties in formulation, particularly when intravenous solutions are needed. A number of approaches for preparing intravenous compositions of sparingly or poorly water-soluble drugs are available. These methods include: physio-chemical solubilization techniques such as micellar solubilization by means of surface-active agents, formation of complexes, solid solutions and solid dispersions by means of the use of suitable polymers; use of various co-solvent systems; and use of the formation of complexes by the addition of chelating agents such as citric acid, tartaric acid, amino acids, thioglycolic acid, and edetate sodium. Other approaches are the use of buffering agents such as acetate, citrate, glutamate and phosphate salts. However, buffers and chelating agents have been implicated in adverse effects such as nephrotoxicity and renal tubular necrosis. Each of these methods has its inherent limitations and the solubility levels that can be achieved with the methods discussed above are still insufficient to make their use in intravenous commercial products.

U.S. Pat. No. 7,148,211 describes parenteral formulation of several representative therapeutic agents including anti-platelet agents such as clopidogrel. It is described in U.S. '211 how a parenteral formulation can be prepared with the lipophilic drug clopidogrel, a non-ionic solubilizer polysorbate 20 present at a concentration of about 0.05% to about 5% with or without the lipophilic antioxidant butylated hydroxytoluene (BHT) present at a concentration of about 20 to about 2000 ppm. Additionally ethanol can be present at a concentration of 0 to 30% with or without an aqueous vehicle.

In another example, Acusphere has described their Imagify® technology that uses perfluorobutane polymer microspheres for dissolving water-insoluble drugs such as clopidogrel.

Sanofi-Aventis atents U.S. Pat. Nos. 5,576,328 and 5,989,578 describe the use of parenteral preparations of clopidogrel and a pharmaceutically acceptable acid addition salt together with a pharmaceutically acceptable carrier.

For parenteral, intranasal, or intramuscular administrations, aqueous suspensions and isotonic and injectable solutions are used that contain dispersing agents and/or wetting agents that are pharmacologically compatible (e.g., propylene glycol or butylene glycol). The active ingredient is provided in the form of a complex with cyclodextrin, (e.g., α, β, or gamma cyclodextrin or 2-hydroxypropyl-β-cyclodextrin).

US Patent Publication 2006/0171948 by Regeneron Pharmaceuticals describes administration by subcutaneous or IV injection or infusion of antiplatelet agents such as clopidogrel. This patent publication describes the use of microspheres for sterile filling and using a technology from CyDex Corporation that employs cyclodextrin and captisol for solubilization.

There still is a need for pharmaceutical formulations of lipophilic anti-platelet agents such as clopidogrel that overcome the limitations of the above described approaches.

SUMMARY OF THE INVENTION

In an aspect, the present invention provides a novel clopidogrel formulation that can be sterilized using filtration or heat and that is acceptable for intravenous administration to man.

In another aspect, the present invention provides a novel process for preparing a formulation of solubilized clopidogrel.

These and other aspects, which will become apparent during the following detailed description, have been achieved by the inventors' discovery that dextrose solution can be useful in solubilizing clopidogrel.

DETAILED DESCRIPTION OF THE INVENTION

Intravenous formulations of clopidogrel in parenterally acceptable solvents are useful for the treatment of emergency ischemic conditions such as acutely developing myocardial infarction, acute coronary syndrome (ACS), or when coronary angioplasty and/or coronary stenting is to be undertaken. It can be beneficial for IV formulations of clopidogrel in parenterally acceptable solvents to be stable and remain clear and colorless for a period of at least one year before use.

In a continuing search for solvents capable of dissolving clopidogrel, it was discovered that $D_{50}W$ (50% dextrose in water, 500 mg/mL dextrose (glucose) in water) was surprisingly capable of forming a stable solution of clopidogrel at room temperature and at 40°. It was surprising as $D_5W$ (5% dextrose in water) was not capable of forming a stable solution of clopidogrel.

Thus, in an aspect, the present invention provides a parenteral formulation, comprising:
 a. clopidogrel;
 b. 100-20% by volume $D_{50}W$; and,
 c. 0-80% by volume aqueous buffer.

In another aspect, the present invention provides a parenteral formulation, wherein the pH of the formulation is from 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4., 5.5, 5.6, 5.7, 5.8, 5.9, to 6.0. Additional examples of the pH include (a) 2.2, (b) 2.5, (c) 3.5, (d) 4.2, (e) 4.5, (f) 2.2-4.5, and (g) 2.2-6.0.

If an optional, aqueous buffer is desired, the buffer selected is dependent upon the pH desired. Thus any buffer suitable for administration and effective within a desired pH can be used. Examples of aqueous buffers include any of a variety of organic and inorganic acids, which include acetate, adipate, azelate, borate, citrate, formate, glutamate, glutarate, lactate, malonate, maleate, oxalate, phosphate (mono and dibasic), pimelate, suberate, sebacate, succinate, tartrate, and urate. Other aqueous buffers may include MES (2-(N-Morpholino)ethanesulfonic acid), BIS-TRIS (2,2-Bis(hydroxymethyl)-2,2',2"-nitrilotriethanol), ADA, ACES (N-(2-Acetamido)-2-aminoethanesulfonic acid), PIPES (1,4-Piperazinediethanesulfonic acid), BES (N,N-Bis(2-hydroxyethyl)-2-aminoethanesulfonic acid), MOPS (3-(N-Morpholino)propanesulfonic acid), HEPES (4-(2-Hydroxyethyl)piperazine-1-ethanesulfonic acid), and TES (2-[(2-Hydroxy-1,1-bis(hydroxymethyl)ethyl)amino]ethanesulfonic acid).

In another aspect, the present invention provides a parenteral formulation, comprising:

a. clopidogrel;
b. 100, 95, 90, 85, 80, 75, 70, 65, 60, 55, 50, 45, 40, 35, 30, 25 to 20% by volume D50W; and,
c. 0, 5, 10, 15, 20, 25, 30, 25, 40, 45, 50, 55, 60, 65, 70, 75, to 80% by volume aqueous buffer.

In another aspect, the present invention provides a parenteral formulation, comprising:
a. clopidogrel;
b. 100-20% by volume $D_{50}W$; and,
c. 0-80% by volume acetate buffer.

In another aspect, the present invention provides a parenteral formulation, wherein 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, to 150 mg/mL of clopidogrel is present in the formulation. Further examples of the concentration of clopidogrel include 75 mg/mL and 150 mg/mL.

In another aspect, the present invention provides a parenteral formulation, comprising:
a. 75 to 150 mg/mL clopidogrel; and,
b. 100% by volume $D_{50}W$.

In another aspect, the formulation has a pH of from 2.2-4.5.

In another aspect, the present invention provides a parenteral formulation, comprising:
a. 75 mg/mL clopidogrel; and,
b. 100% by volume $D_{50}W$.

In another aspect, the present invention provides a parenteral formulation, comprising:
a. 150 mg/mL clopidogrel; and,
b. 100% by volume $D_{50}W$.

In another aspect, the present invention provides a parenteral formulation, comprising:
a. 75 to 150 mg/mL clopidogrel;
b. 20% by volume $D_{50}W$; and,
c. 80% by volume buffer.

In another aspect, the buffer is aqueous acetate buffer (i.e., acetate buffer).

In another aspect, the formulation has a pH of from 2.2-4.5.

In another aspect, the present invention provides a parenteral formulation, comprising:
a. 75 mg/mL clopidogrel.

In another aspect, the present invention provides a parenteral formulation, comprising:
a. 150 mg/mL clopidogrel.

The parenteral formulation of the present invention can be administered as is or can be diluted prior to administration. Dilution can be advantageous to reduce the concentration of a formulation. For example, a parenteral formulation of the present invention can be diluted with $D_5W$ sterile solution for parenteral injection. The parenteral formulation of the present invention can be injected IV by a syringe filled from a vile, from a pre-filled syringe, or administered from an IV infusion set or from an IV bag or bottle stored sterilely for IV administration. The bag or infusion set may contain clopidogrel in $D_{50}$ only or at varying concentrations of clopidogrel in dextrose and water (e.g., $D_{5, 10, 15, 20, 25, 30, 35, 40, 45}$).

In another aspect, the present invention provides a method of treating emergency ischemic conditions, comprising: administering a therapeutically effective amount of a formulation of the present invention to a patient in need thereof. Examples of emergency ischemic conditions include acutely developing myocardial infarction and acute coronary syndrome (ACS).

In another aspect, the present invention provides a method of treating a patient undergoing coronary angioplasty and/or coronary stenting, comprising: administering a therapeutically effective amount of a formulation of the present invention to a patient in need thereof is to be undertaken.

Clopidogrel refers to clopidogrel bisulfate.

All references cited herein are hereby incorporated in their entirety herein by reference.

Other features of the invention will become apparent in the course of the following descriptions of exemplary aspects that are given for illustration of the invention and are not intended to be limiting thereof.

EXAMPLES

Example 1

To 75 mg of clopidogrel, 1 mL of dextrose 50% solution ($D_{50}W$) was added and the mixture stirred gently until a clear and colorless solution was obtained (heating is unnecessary). The pH of the solution was 2.2.

The 75 mg/mL clopidogrel solution in $D_{50}W$ was kept at room temperature for 6 weeks without observed change.

This solution was also kept at 40° for 6 weeks without observed change.

Similar results were obtained using 150 mg of clopidogrel instead of 75 mg.

Also, the pH can be changed up to 4.2 without affecting its stability.

Example 2

To 75 mg of clopidogrel, 1 mL of dextrose 50% solution ($D_{50}W$) was added and the mixture stirred gently until a clear and colorless solution was obtained.

To 0.5 mL of the clopidogrel solution was added 2 mL of pH 2.5 acetate buffer (prepared from 0.1 N glacial acetic acid and pH adjustment with 1.0 N NaOH).

The 15 mg/mL clopidogrel solution in $D_{50}W$/acetate buffer was kept at room temperature for 4 weeks without observed change.

This solution was also kept at 40° for 4 weeks without observed change.

Example 3

To 75 mg of clopidogrel, 1 mL of dextrose 50% solution ($D_{50}W$) was added and the mixture stirred gently until a clear and colorless solution was obtained.

To 0.5 mL of the clopidogrel solution was added 2 mL of pH 3.5 acetate buffer.

The 15 mg/mL clopidogrel solution in $D_{50}W$/acetate buffer (pH 3.5) was kept at room temperature for 4 weeks without observed change.

This solution was also kept at 40° for 4 weeks without observed change.

Numerous modifications and variations of the present invention are possible in light of the above teachings. It is therefore to be understood that within the scope of the appended claims, the invention may be practiced otherwise that as specifically described herein.

What is claimed is:
1. A parenteral formulation, comprising;
a. clopidogrel;
b. 100-20% by volume $D_{50}W$ (dextrose 50% solution); and,
c. 0-80% by volume aqueous buffer.

2. The parenteral formulation of claim 1, wherein 1.0 mg/mL to 150 mg/mL of clopidogrel is present in the formulation.

3. The parenteral formulation of claim 1, wherein 150 mg/mL of clopidogrel is present in the formulation.

4. The parenteral formulation of claim 1, wherein 75 mg/mL of clopidogrel is present in the formulation.

5. The parenteral formulation of claim 1, wherein 15 mg/mL of clopidogrel is present in the formulation.

6. The parenteral formulation of claim 1, wherein 100% by volume $D_{50}W$ is present in the formulation.

7. The parenteral formulation of claim 1, wherein 20% by volume $D_{50}W$ is present in the formulation.

8. The parenteral formulation of claim 1, wherein 80% by volume aqueous buffer is present in the formulation.

9. The parenteral formulation of claim 1, wherein the aqueous buffer is selected from: acetate, adipate, azelate, borate, citrate, formate, glutamate, glutarate, lactate, malonate, maleate, oxalate, phosphate monobasic, phosphate dibasic, pimelate, suberate, sebacate, succinate, tartrate, and urate.

10. The parenteral formulation of claim 1, wherein 20% by volume $D_{50}W$ and 80% by volume aqueous acetate buffer are present in the formulation.

11. The parenteral formulation of claim 1, wherein the pH of the formulation is from 2.2-6.

12. The parenteral formulation of claim 1, wherein the pH of the formulation is from 2.2-4.5.

13. The parenteral formulation of claim 1, wherein the pH of the formulation is 2.2.

14. The parenteral formulation of claim 1, wherein the pH of the formulation is 2.5.

15. The parenteral formulation of claim 1, wherein the pH of the formulation is 3.5.

16. The parenteral formulation of claim 1, wherein the pH of the formulation is 4.5.

17. The parenteral formulation of claim 1, comprising:
   a. 75 to 150 mg/mL clopidogrel; and,
   b. 100% by volume $D_{50}W$.

18. The parenteral formulation of claim 17, comprising:
   a. 75 mg/mL clopidogrel; and,
   b. 100% by volume $D_{50}W$.

19. The parenteral formulation of claim 17, comprising:
   a. 150 mg/mL clopidogrel; and,
   b. 100% by volume $D_{50}W$.

20. The parenteral formulation of claim 1, comprising:
   a. 75 to 150 mg/mL clopidogrel;
   b. 20% by volume $D_{50}W$; and,
   c. 80% by volume acetate buffer.

* * * * *